(12) United States Patent
Kessels

(10) Patent No.: US 6,359,172 B1
(45) Date of Patent: Mar. 19, 2002

(54) METHOD OF PREPARING 2- AND 4-HYDROXYMANDELIC ACID

(75) Inventor: Raoul Kessels, Barcelona (ES)

(73) Assignee: Gerard Kessels Sociedad Anonima, S.A., Puerto Rey (Vera) Almeria (ES)

( * ) Notice: Subject to any disclaimer, the term of this patent is extended or adjusted under 35 U.S.C. 154(b) by 0 days.

(21) Appl. No.: 09/396,397

(22) Filed: Sep. 15, 1999

(30) Foreign Application Priority Data

Sep. 15, 1998 (NL) ............................................. 1010090

(51) Int. Cl.⁷ ................................................ C07C 59/50
(52) U.S. Cl. ...................................... 562/475; 562/470
(58) Field of Search ................................. 562/470, 475

(56) References Cited

U.S. PATENT DOCUMENTS

| | | | | |
|---|---|---|---|---|
| 4,198,523 A | * | 4/1980 | Copeland |
| 4,368,334 A | * | 1/1983 | Dales |
| 4,978,784 A | * | 12/1990 | Christidis |
| 5,248,816 A | * | 9/1993 | Shuttleworth et al. |
| 5,354,897 A | * | 10/1994 | Schouteeten et al. |

FOREIGN PATENT DOCUMENTS

| | | | |
|---|---|---|---|
| JP | 355102537 | * | 8/1980 |
| KR | 95-5766 | * | 5/1995 |
| KR | 9505766 | * | 5/1995 |

OTHER PUBLICATIONS

Organic Chemistry—second edition. Edited by Morrison and Boyd. Published by Allyn and Bacon, Inc. 1966. p346.*
Chemical Abstracts 2000:455498 of KR 9505766 (May–1995).*

* cited by examiner

Primary Examiner—James O. Wilson
Assistant Examiner—Zachary C. Tucker
(74) Attorney, Agent, or Firm—Eugene C. Rzucidlo; Greenberg Traurig, LLP

(57) ABSTRACT

The invention relates to a method of preparing 2- and 4-hydroxymandelic acid by condensing glyoxylic acid with phenol. The glyoxylic acid is reacted with phenol, after which the formed reaction mixture or the phenol, the 2- and 4-hydroxymandelic acid respectively are elution-separated in a column comprising an anion exchange resin, wherein first the excess phenol is separated, followed by the separation of the 4-hydroxymandelic acid and finally the 2-hydroxymandelic acid, both in the form of acid and salt, depending on the eluent used.

24 Claims, No Drawings

METHOD OF PREPARING 2- AND 4-HYDROXYMANDELIC ACID

The invention relates to a method of preparing 2- and 4-hydroxymandelic acid by condensing glyoxylic acid with phenol.

Hydroxymandelic acids are very valuable compounds as they are versatile starting materials for the production of compounds that may be used in various fields such as fine chemicals technology, pharmaceutical chemistry and agricultural chemistry. 4-Hydroxymandelic acid is an intermediate product for the preparation of 4-hydroxybenzyl aldehyde, used in the synthesis of fine chemicals; 4-hydroxyphenyl acetic acid used in the synthesis of the pharmaceutical compound atenolol; 4-hydroxyphenylglycine used in the preparation of the antibiotic amoxycilline, etc. 2-Hydroxymandelic acid is an intermediate product for the preparation of the agrochemical compound ethylene diamine-N,N'-bis(2-hydroxyphenyl acetic acid); 2-hydroxyphenyl acetic acid, used in pharmaceutical compounds; 2-hydroxyphenyl-2-oxoacetic acid methyl ester used in the preparation of fungicides, etc.

The method of preparing 2- and 4-hydroxymandelic acid by condensation of glyoxylic acid with phenol has long been known. Under different conditions glyoxylic acid is condensed with an excess of phenol yielding a mixture of both mandelic acids. The excess of phenol is normally extracted, after acidification of the reaction mixture with a water-immiscible solvent. Subsequently, the 4-hydroxymandelic acid is separated in the form of a salt in the usual manner, while the 2-hydroxymandelic acid is usually not isolated.

The Belgian patent specification 867,287 describes the condensation of glyoxylic acid with phenol in a homogenous system in the presence of sodium or potassium hydroxide. The 4-hydroxymandelic acid is isolated in the form of a salt by adding an inorganic salt to the reaction mixture. Similarly, the U.S. patent specification 4,408,070 describes the homogenous condensation of glyoxylic acid with excess phenol, by using sodium hydroxide. The excess phenol is separated after neutralization by means of steam distillation or extraction with 1,2-dichloroethane, after which the 4-hydroxymandelic acid is precipitated in the presence of sodium acetate. In the known method wherein a salt is added in order to salt out the product, contamination with salt occurs while at the same time a salt-saturated mother liquor is left which is contaminated with by-products formed during the reaction. In the above-mentioned cases the yields of isolated product do not exceed 61%.

The European patent application EP-0,024,181 further describes the condensation of glyoxylic acid with phenol in a homogenous system in the presence of sodium or potassium hydroxide. The reaction mixture is subsequently acidified and the excess of phenol is extracted with methyl isobutyl ketone. The reaction mixture is further acidified and subjected to a second extraction with methyl isobutyl ketone. Subsequently the 4-hydroxymandelic acid is precipitated in a 50–73% yield as a salt from the extract, the remaining part of the organic material, i.e. all the 2-hydroxy isomer and part of the 4-hydroxy isomer, is distributed between the aqueous phase and the solvent phase.

The European patent specification EP-0,368,696 describes the condensation of a glyoxylic acid with phenol in the presence of a water-insoluble amine, to form a 12:84 mixture of 2- and 4-hydroxymandelic acid respectively. Then the excess of phenol is extracted with 1,1-dimethyl-1-methoxypropane. Only 70–74% of the paraisomer, 4-hydroxymandelic acid, is isolated leaving a non-separable mixture of approximately 1:1 2- and 4-hydroxymandelic acid.

Both the methods described in EP-0,024,181 and EP-0,368,696 use two alkaline compounds to obtain the desired mandelic acid; one to perform the reaction and a different one to isolate the product. From a technical and economical point of view, it would be preferable to use only one base, namely the base by means of which the suitable salt of the mandelic acid can be obtained.

Attempts have been made to produce only 2-hydroxymandelic acid. Hoefnagel et al. describe in Recl. Trav. Chim. Pays-Bas 107, 242–247 (1988) the reaction of glyoxylic acid with phenol using metal ion catalysis, to produce 2-hydroxymandelic acid in modest yields together with 4-hydroxymandelic acid. The products were, however, not isolated.

The European patent application EP-0,556,084 also uses trivalent metal ion catalysis but in the presence of insoluble amines, to obtain a solution comprising a mixture of 2- and 4-hydroxymandelic acids, wherein the 2-hydroxymandelic acid is present in excess with yields varying from 59–87%. A water-immiscible solvent is used to extract the excess of phenol, but none of the products is isolated. A disadvantage of these methods is the presence of high-valency metal ions in the final product, and the fact that the catalyst is not reusable. The product was never isolated, possibly due to its extremely high solubility in water, and it is proposed to use the impure solution directly in subsequent reactions.

The solvent extraction of phenol from water, common to all processes, is a problem in itself, as is apparent from the myriad of systems and processes that have been developed for this purpose. Because of its high toxicity, the phenol must be completely eliminated from the effluent stream. Typical examples are the simple extraction with additional salts, polyhydric alcohols or polyglycol ethers; the single or multi solvent counter-current continuous extraction; the two-solvent extraction distillation; the supported-liquid membrane processes; the extraction device with two membranes plus one solvent and a stripping solution; removal by pervaporation, etc. The use of these complicated and specialized systems is necessary because of the high water affinity of phenol. Phenol is best extracted with solvents that also have a high affinity for water, but in that way too much solvent is lost in the aqueous phase. This makes it necessary to add salts or a water-immiscible solvent when phenol is to be extracted with a partially water-soluble solvent. Another general disadvantage of phenol extraction is the necessity of acidifying the mother liquor prior to extraction to avoid to ionized phenoxide form present in the aqueous phase during extraction. This is especially necessary when the mother liquor is alkaline, as with the condensation of glyoxylic acid with phenol.

The above-mentioned methods always result in a mixture of 2- and 4-hydroxymandelic acids the specific formation of only one isomer is not possible. The complete separation of these isomeric mixtures is not realized, and their relative quantities can only be determined by means of analytical methods.

WO 94/14746 discloses a method of separating both isomers by means of the solvent extraction of a solid mixture of 2- and 4-hydroxymandelic acid alkali metal salts. The solid mixture is extracted with one solvent, acetone, to obtain an enriched fraction of sodium 2-hydroxymandelate, and the remaining solid is again extracted with a solvent, this time with ethanol, to obtain an almost pure fraction of sodium 4-hydroxymandelate. It should be pointed out that the hydroxymandelic acids are formed in water, and that this water must be completely eliminated before the separation can be performed. Another disadvantage is that two solvents are used for the separation of both isomers, for which an adequate recovery system must be used. Moreover, the solid-liquid extraction is not at all efficient, as one solid can be incorporated in the other, with the result that it is not subjected to extraction.

It would be advantageous if both isomers could be separated directly from the reaction mixture in which they are formed, thereby avoiding the evaporation of water and the use of flammable and/or toxic solvents.

It is the object of the present invention to provide a method of preparing 2- and 4-hydroxymandelic acid, wherein the above-mentioned disadvantages are effectively removed. To this end the present invention provides a method of preparing 2- and 4-hydroxymandelic acid by condensing glyoxylic acid with phenol, characterized in that the glyoxylic acid is reacted with phenol, after which the phenol, the 2- and 4-hydroxymandelic acid respectively are elution-separated in a column comprising an anion exchange resin, wherein first the excess phenol is separated, followed by the separation of the 4-hydroxymandelic acid in the form of acid or salt and finally the 2-hydroxymandelic acid, also in the form of acid or salt, depending on the eluent.

Surprisingly it has been shown that if the reaction of glyoxylic acid is performed with an excess of phenol in the presence of an anion exchange resin, i.e. in the solid phase, a mixture of 2- and 4-hydroxymandelic acid is obtained, wherein the total yield based on the glyoxylic acid used, is 100%. This reaction may be performed in a stirred reaction vessel comprising the particle anion exchange resin, or in a fluidized bed in a column. To separate the various components, the reaction mixture is transferred into a column.

Surprisingly it has been shown that the 2- and 4-hydroxymandelic acid formed and distributed uniformly over the resin, can be desorbed selectively from the resin. This makes it possible to completely separate the two isomers from the reaction medium.

It has also been shown that if a solution comprising 2- and 4-hydroxymandelic acid or their salts are contacted with an anion exchange resin, the 2-hydroxy isomer is selectively adsorbed, while the 4-hydroxy isomer remains in solution. This selective adsorption makes it possible to easily and completely separate both isomers from a solution.

Preferably the reaction is performed in a column wherein the anion exchange resin is fluidized, for example, by using the simulated fluidized bed technique. This avoids the use of reactors and extra separation devices.

According to the invention it is advantageous if the phenol is used in a 1.05 to 10 equivalent excess in relation to the glyoxylic acid, and preferably in an excess of 1.1 to 6 equivalents.

Usually the reaction is performed at a temperature of 10–95° C., preferably at 30–70° C.

According to the present invention, usually an anion exchange resin is used comprising 1–5 and preferably 1.1–2.5 equivalents of anion exchange sites with respect to the amount of glyoxylic acid used. Preferably the number of anion exchange sites that the anion exchange resin possesses is equal to the total number of moles of 2-hydroxymandelic acid present in the mixture.

According to the preferred embodiment the anion exchange resin possesses one or various types of functional groups such as $NR_1R_2R_3$, $N^+R_1R_2R_3R_4$, $R_1R_2NNR_3R_4$, $R_1R_2NN^+R_3R_4R_5$, $R_1R_2NC(NR_5)NR_3R_4$, $[R_1R_2NC(NR_5R_6)NR_3R_4]^+$, R1–R6 substituted C2–C9 heterocyclic group comprising nitrogen, or R1–R6 substituted C2–C9 perhydroheterocyclic group comprising nitrogen when $R_1$, $R_2$, $R_3$, $R_4$, $R_5$, and $R_6$ possibly are or are not the same, and represent hydrogen or alkyl, hydroxyalkyl, benzyl, aryl or substituted aryl.

According to another feature of the present invention, the excess phenol is selectively eluted from the resin by means of an eluent. Preferably this eluent is hot water, steam, a water-miscible solvent or a water-immiscible solvent. The water-miscible solvent may be, for example, methanol, ethanol, ethyleneglycol, propanol, a $C_3$–$C_6$ alcohol, acetone, methylethylketone, acetonitrile, proprionitrile, dimethylsulphoxide, formamide, dimethylformamide or binary or multiple mixtures thereof.

The water-immiscible solvent may, for example, be a methyl formate, ethyl formate, methyl acetate, ethyl acetate, a $C_4$–$C_8$ ester, diethyl ether, tert-butyl methyl ether, isopropyl ether, a $C_4$–$C_8$ ether, a $C_4$–$C_6$ ketone, dichloromethane, chloroform, dichloroethane, chlorobenzene or another chlorinated solvent, or pentane, hexane, cyclohexane, toluene, or another hydrocarbon or a binary or multiple mixture thereof.

In accordance with the invention the hydroxymandelic acids of the resin are usually eluted by means of an acid, base or a salt solution. The acid may, for example, be hydrochloric acid, sulphuric acid, $H_2CO_3$, carbon dioxide, sulphamic acid, phosphoric acid, boric acid, nitric acid, formic acid, acetic acid, chloroacetic acid, propionic acid, methanosulphonic acid, benzenesulphonic acid, p-toluenesulphonic acid, a $C_1$–$C_{14}$ organic acid or a mixture thereof.

The base may, for example, be sodium hydroxide, potassium hydroxide, lithium hydroxide, ammonia, hydrazine, calcium hydroxide, methylamine, ethylamine, aniline, ethylenediamine, triethylamine, tetra ethyl ammonium hydroxide, a $C_2$–$C_{18}$ amine, a $C_4$–$C_{18}$ ammonium hydroxide, sodium methoxide, potassium methoxide, a $C_1$–$C_4$ organic base or a mixture thereof.

The salt may, for example, be sodium bicarbonate, potassium bicarbonate, ammonium bicarbonate, sodium carbonate, potassium carbonate, ammonium carbonate, or a salt formed by the above acids and bases. According to another feature of the present invention the solution is a solution on water basis, or on solvent basis.

According to a favourable embodiment in accordance with the invention, the 2-hydroxymandelic acid and the 4-hydroxymandelic acid are separated by means of selective desorption. In accordance with a preferred embodiment the 4-hydroxymandelic acid and the 2-hydroxymandelic acid are desorbed successively, using a desorbant. In accordance with another preferred embodiment the 2-hydroxymandelic acid and 4-hydroxymandelic acid are selectively desorbed by using two is different desorbants.

In accordance with another embodiment of the present invention a solution of 2-hydroxymandelic acid and 4-hydroxymandelic acid in the form of acids and salts are separated by means of elution over a column of anion exchange resin. The salts occur in the form of sodium, potassium, lithium, ammonium, methyl ammonium, tetramethyl ammonium, $C_2$–$C_{18}$ ammonium, ethylene diamine, magnesium, calcium, group II metal cation salt.

The reaction according to the invention is performed on an anion exchange resin, wherein the resin preferably comprises tertiary or quaternary amino groups or a combination of both, or other anion exchange functionalities, attached to an arbitrary polymer. The anion exchange resin may be contained in a stirred reaction vessel or in a column and is covered with water. The amount of water may vary greatly and has no effect on the reaction. The resin comprises preferably 1 to 5 equivalents of anion exchange sites in relation to the mount of glyoxylic acid used. An excess of phenol is added to the resin, the required quantity being 1.1 to 10 equivalents per equivalent glyoxylic acid used; and 1 equivalent of glyoxylic acid is distributed uniformly over the anion exchange resin. The condensation reaction is performed at a temperature between 10 and 95° C., preferably between 30 and 70° C.

After the appropriate reaction time, which depends on the conditions employed such as, in particular, temperature and type of resin, the water is decanted and the phenol is desorbed from the resin. The decanted water which contains some phenol may be reused in the next condensation reaction. The desorption treatment is preferably performed in a column. The phenol is easily and completely desorbed by means of a solvent, hot water, steam, or a mixture thereof. The solvent may be water-miscible or water-immiscible, or mixtures of both types.

Steam, hot water, or mixtures thereof may also be used according to the invention.

Combinations of the above-mentioned desorbants are also suitable.

The phenol/solvent mixture can easily be separated into its components by the known means, for example, by distillation. The recovered phenol may be reused for the condensation with glyoxylic acid. In the event that the phenol is desorbed with hot water or steam, the phenol/water mixture obtained may immediately be reused in the method.

When the phenol desorption is completed, the mandelic acids are desorbed by means of an acidic solution, an alkaline solution or a saline solution, yielding the 2-and 4-hydroxymandelic acids in the required acid or salt form. The solution for the desorption of the mandelic acids may be based on water or on solvent, the above-mentioned solvents being suitable for this purpose. During desorption the 4-hydroxy isomer is collected first, followed by the 2-hydroxy isomer. optionally two different desorbants may be used to obtain both isomers. The 2- and 4-hydroxymandelic acids or salts may also be desorbed as a mixture.

The mandelic acids or salts can be isolated by eliminating the water or solvent by the conventional methods, for example by vacuum distillation, spray-drying, etc. None of these processes changes the resin so that it may be reused unconditionally for the same method.

Any solution of 2- and 4-hydroxymandelic acid in the form of free acids or salts, obtained by the invention as described or by one of the above-mentioned prior art methods, may be used directly in the separation process.

Separation according to the invention is performed on an anion exchange resin, the resin optionally being of the same kinds as used in the condensation reaction. Preferably the number of anion exchange sites that the resin comprises is equal to the number of moles of 2-hydroxymandelic acid present in the mixture, up to 2.5 equivalents of anion exchange sites in relation to the total number of moles of mandelic acid present in the mixture. The most suitable amount depends on the form of the mandelic acids (free acids, type of salt) and the type of resin.

The mixtures of 2- and 4-hydroxymandelic acids that can be separated according to the invention are 5:95 to 95:5 mixtures in the form of free acids, alkaline salts, ammonium salts, alkylammonium salts, or group II metal salts.

The hydroxymandelic acids or salts can be isolated in pure form from the obtained solutions by means of the conventional methods, for example, by vacuum distillation, spray-drying, etc., or can be directly used as solutions in other applications.

The invention will now be further elucidated by means of a number of non-limitative exemplary embodiments. All analyses in the following examples were performed using the HPLC technique described by Hoefnagel et al. in Recl. Trav. Chim. Pays-Bas 115, 355 (1996).

EXAMPLE 1

10 l of a granular, commercially available anion exchange resin, macroreticular and functionalized with tetra alkyl ammonium groups, having 1.2 equivalent anion exchange sites per liter resin, were brought into a stirred reaction vessel and covered with water. The temperature was adjusted to 45° C., and under stirring 2.51 kg (26.7 moles) of phenol were added. Under stirring 1 kg (6.7 moles) of a 50% glyoxylic acid solution in water was added in 20 min. The reaction mixture was maintained at 45° C. for 8 hours. The mixture was transferred to the standard chromatography column and the water was decanted. The water fraction was reserved for a following reaction. HPLC analysis of the water fraction indicated that it contained 0.2 kg of phenol. 13 l of tert-butylmethylether were passed through in 30 min. which was collected separately and analyzed by means of HPLC. Analysis showed that it contained 1.7 kg of phenol. Then 15.3 kg of a 5% $Na_2CO_3$ solution was passed through in 60 min. 18.7 kg of solution was collected and the HPLC analysis showed a 7.4% concentration of sodium hydroxymandelate monohydrate (99,5% yield based on glyoxylic acid) of which 81% was the 4-hydroxy isomer and 19% the 2-hydroxy isomer.

EXAMPLE 2

10 l of a commercially available anion exchange resin, gel type and functionalized with trialkalylamine groups, having 1.5 equivalent anion exchange sites per liter resin, was brought into a stirred reaction vessel and covered with water. Under stirring 2.47 kg (26.3 moles) of phenol was added, and the temperature was adjusted to 35° C. Under stirring 1.11 kg (7.5 moles) of a 50% glyoxylic acid solution in water was added in 20 min. The reaction mixture was maintained at 35° C. for 12 hours. The mixture was transferred to the standard chromatography column, and the water was decanted. The water fraction was reserved for a next reaction. HPLC analysis of the water fraction indicated that it contained 0.3 kg of phenol. 14 l of methanol was passed through in 30 min., which was collected separately and analyzed with HPLC. Analysis indicated that it contained 1.5 kg of phenol. Then 7.7 kg of a 5% ammonia solution was passed through in 60 min. 11.0 kg of solution was collected, HPLC analysis indicating a 13.8% concentration of ammonium hydroxymandelate monohydrate. The solution was spray-dried and 1.51 kg of a white solid was obtained. Analysis of the solid indicated that it comprised 83% 4-hydroxymandelic acid ammonium salt crystallized with 1 molecule of water, and 17% 2-hydroxymandelic acid ammonium salt crystallized with 1 molecule of water. The total yield based on glyoxylic acid was 99.0%.

The methanol was separated from the methanolic fraction through a normal distillation. Hereby 13 liters of methanol was collected. The residue weighed 1.6 kg and was analyzed by means of HPLC, and was shown to comprise 1.4 kg of phenol. Karl Fisher analysis of the residue determined a water content of 13%.

EXAMPLE 3

The 1.51 kg mixture of 2- and 4-ammonium hydroxymandelates obtained in Example 2 was dissolved in 6.88 kg water, and was eluted over a column comprising 3.5 l of a macroreticular anion exchange resin, functionalized with 3 alkylamino groups containing 1.8 equivalent anion exchange sites per liter resin. After passing all the solution through the column, the column was washed with 1.52 kg of 7% ammonia to desorb all the 4-hydroxymandelic acid. The collected fraction was evaporated until dry, yielding 1.24 kg of 4-hydroxymandelic acid ammonium salt, crystallized with 1 molecule of water. The yield based on the 4-hydroxymandelic acid present in the mixture was 99.7%.

5.04 kg of 5% NaOH was passed through the column. The collected solution was passed through a strongly acidic cation exchange resin containing 5.05 equivalent acid exchange sites to absorb the sodium hydroxide excess. The solution was evaporated until dry providing 0.26 kg of 2-hydroxymandelic acid sodium salt, crystallized with 1 molecule of water. The yield based on the 2-hydroxymandelic acid contained in the mixture was 99.4%.

EXAMPLE 4

10 l of an anion exchange resin, macroreticular and functionalized with trialkyl, hydroxyalkylammonium groups, having 1.8 equivalent anion exchange sites per liter resin, was brought into a column and covered with the water fraction from Example 2. The resin bed was fluidized and the 1.73 kg distillation residue from Example 2 and 0.51 kg (24.5 moles) of phenol was added, and the temperature was adjusted to 65° C. While the resin bed was fluidized, 1.21 kg (8.2 moles) of a 50% glyoxylic acid solution in water was added in 20 min. The reaction mixture was maintained at 65° C. for 6 hours. As soon as the reaction was completed the water was decanted. The water fraction was reserved for the next reaction. HPLC analysis of the water fraction indicated that it contained 0.1 kg of phenol. 12 l of chloroform was passed through in 30 min., and collected separately for analysis by means of HPLC. Analysis indicated that it contained 1.5 kg of phenol. 17.2 kg of a 4% HCl-solution was passed through in 60 min. The first 16.1 kg of solution collected was carefully evaporated until dry, maintaining the temperature below 50° C. whereby 1.16 kg of a white solid was obtained. Analysis indicated pure 4-hydroxymandelic acid crystallized with 1 molecule of water. The yield based on glyoxylic acid was 76.9%.

A second fraction of 4.3 kg of solution was collected and carefully evaporated until dry, maintaining the temperature below 35° C., and 0.29 kg of an oil was obtained. Analysis indicated 98% 2-hydroxymandelic acid hydrate. The yield based on glyoxylic acid was 18.8%.

EXAMPLE 5

Example 1 of European Patent application EP 0,556,084 was reproduced, and after elimination the amine and the excess phenol, and converting the mandelic acids to potassium salts, a solution comprising 281 g (1,25 moles) of 2-hydroxymandelic acid potassium salt monohydrate and 45 g (0.20 moles) 4-hydroxymandelic acid potassium salt monohydrate was obtained.

The solution was passed through a column containing 0.95 l of an anion exchange resin, gel type and functionalized with tetra alkyl ammonium groups, having 1.6 equivalent anion exchange sites per liter resin. The column was washed with water, and the collected solution was neutralized by means of a strongly acidic cation exchanger. The collected fraction was evaporated until dry, and 41.6 g of 4-hydroxymandelic acid potassium salt monohydrate was obtained. Subsequently, 1.33 kg of an 8% potassium methoxide solution was passed through the column and the collected solution was evaporated until dry. This yielded 257 g of 2-hydroxymandelic acid potassium salt, solvent free.

EXAMPLE 6

10 l of an anion exchange resin, macroreticular and functionalized with trialkylamino groups having 1.6 equivalent anion exchange sites per liter resin, was brought into a column and covered with water. The resin bed was fluidized and 5.31 kg (56.5 moles) of phenol was added and the temperature was adjusted to 60° C.

While the resin bed was fluidized, 1.39 kg (9.41 moles) of a 50% glyoxylic acid solution in water was added in 20 min. The reaction mixture was maintained at 60° C. for 6 hours. As soon as the reaction was completed the water was decanted. The water fraction was reserved for the next reaction. HPLC analysis of the water fraction indicated that it contained 0.4 kg of phenol. 21 l of hot water (95° C.) was passed through in 45 min., collected separately and analyzed by means of HPLC. Analysis indicated that it contained 4.0 kg of phenol. 8.5 kg of a 7% $NH_2Me$.-HCl solution was passed through in 60 min. The first 9.7 kg collected was evaporated until dry and 1.57 kg of 4-hydroxymandelic acid methyl ammonium salt monohydrate was obtained. The yield based on glyoxylic acid was 77.0%.

The subsequent 2.8 kg solution collected from the column was evaporated until dry and 0.44 kg of 2-hydroxymandelic acid methyl ammonium salt monohydrate was obtained. The yield based on glyoxylic acid was 21.6%.

Total yield of mandelic acids: 98.6%.

EXAMPLE 7

10 l of an anion exchange resin, macroreticular and having 1.7 equivalent anion exchange sites per liter resin, of which 80% was trialkylamino, and 20% tetra alkyl ammonium, were brought into a column and covered with water. The resin bed was fluidized and 3.20 kg (34.0 moles) of phenol was added, and the temperature was adjusted to 35° C. While the resin bed was fluidized, 1.32 kg (8.95 moles) of a 50% glyoxylic acid solution in water was added in 20 min. The reaction mixture was maintained at 35° C. for 14 hours. As soon as the reaction was completed, the water was decanted. The water fraction was reserved for the next reaction. HPLC analysis of the water fraction indicated that it contained 0.3 kg of phenol. 12 l of acetone was passed through in 30 min., and collected separately and analyzed by means of HPLC. Analysis indicated that it contained 2.1 kg of phenol. 15.0 kg of 5% NaOH solution was passed through in 60 min. The first 14.9 kg collected was evaporated until dry and 1.49 kg of 4-hydroxymandelic acid sodium salt monohydrate was obtained. The yield based on glyoxylic acid was 80.3%.

The subsequent 3.5 kg collected from the column was evaporated until dry, and 0.35 kg of 2-hydroxymandelic acid sodium salt monohydrate was obtained. The yield based on glyoxylic acid was 18.9%.

Total yield of mandelic acids: 99.2%.

The acetone was separated from the organic fraction by means of a normal distillation. 11 l acetone was obtained. The residue weighed 2.2 kg and was analyzed by means of HPLC, and was shown to contain 2.0 kg of phenol. Karl Fisher analysis of the residue determined a water content of 11%.

EXAMPLE 8

The same 10 l anion exchange resin from Example 7, still in the column, was covered with a decanted water fraction from Example 7. The resin bed was fluidized and the distillation residue from Example 7 and 0.9 kg (34.0 moles phenol in total) was added. The temperature was adjusted to 35° C. While the resin bed was fluidized, 1.32 kg (8.95 moles) of a 50% glyoxylic acid solution in water was added in 20 min. The reaction mixture was maintained at 35° C. for 14 hours. As soon as the reaction was completed, the same operation as in Example 7 was performed, and the following fractions were obtained:

a water fraction containing 0.3 kg of phenol an acetone fraction containing 2.1 kg of phenol 1.50 kg of 4-hydroxymandelic acid sodium salt monohydrate 0.34 kg of 2-hydroxymandelic acid sodium salt monohydrate.

The yield of 4-hydroxymandelic acid sodium salt monohydrate based on glyoxylic acid was 80.9%.

The yield of 2-hydroxymandelic acid sodium salt monohydrate based on glyoxylic acid was 18.3%

Total yield of mandelic acids: 99.2%.

What is claimed is:

1. A method of preparing and collecting 2- and 4-hydroxymandelic acid by condensing glyoxylic acid with phenol, characterized in that the glyoxylic acid is reacted with the phenol, after which the phenol and the 2- and 4-hydroxymandelic acid, respectively, are elution-separated and individually collected, said elution separation taking place in a column comprising an anion exchange resin, wherein first the excess phenol is separated, followed by the separation of the 4-hydroxymandelic acid in the form of acid or salt and finally the 2-hydroxymandelic acid, also in the form of acid or salt, depending on the eluents used in the eluent separation.

2. A method according to claim 1, characterized in that the reaction is performed in the presence of the anion exchange resin.

3. A method according to claim 1, characterized in that the reaction is performed in a column wherein the anion exchange resin is fluidized.

4. A method according to claim 1, characterized in that the phenol is used in a 1.05 to 10 equivalent excess in relation to the glyoxylic acid.

5. A method according to claim 1, characterized in that the reaction is performed at a temperature of 10–95° C.

6. A method according to claim 5, characterized in that the reaction is performed at a temperature of 30–70° C.

7. A method according to claim 1, characterized in that the anion exchange resin comprises 1–5 equivalents of anion exchange sites with respect to the amount of glyoxylic acid used.

8. A method according to claim 1, characterized in that the number of anion exchange sites that the anion exchange resin possesses is equal to the number of moles of 2-hydroxymandelic acid present in the mixture, up to 2.5 times in relation to the total number of moles of hydroxymandelic acids present in the mixture.

9. A method according to claim 1, characterized in that the anion exchange resin comprises one or several types of functional groups, such as $NR_1R_2R_3$, $N^+R_1R_2R_3R_4$, $R_1R_2NNR_3R_4$, $R_1R_2NN^+R_3R_4R_5$, $R_1R_2NC(NR_5)$ $NR_3R_4$, $[R_1R_2NC(NR_5R_6)NR_3R_4]^+$, R1–R6 substituted C2–C9 heterocyclic group comprising nitrogen, or R1–R6 substituted C2–C9 perhydroheterocyclic group comprising nitrogen when $R_1$, $R_2$, $R_3$, $R_4$, $R_5$, and $R_6$ possibly are or are not the same, and represent hydrogen or alkyl, hydroxyalkyl, benzyl, aryl or substituted aryl.

10. A method according to claim 1, characterized in that the excess of phenol is selectively eluted from the resin by means of an eluent.

11. A method according to claim 10, characterized in that the eluent is hot water, steam, a water-miscible solvent or a water-immiscible solvent.

12. A method according to claim 10, characterized in that the water-miscible solvent is methanol, ethanol, ethyleneglycol, propanol, a $C_3$–$C_6$ alcohol, acetone, methylethylketone, acetonitrile, proprionitrile, dimethylsulphoxide, formamide, dimethylformamide or binary or multiple mixtures thereof.

13. A method according to claim 10, characterized in that the water-immiscible solvent is a methyl formate, ethyl formate, methyl acetate, ethyl acetate, a $C_4$–$C_8$ ester, diethyl ether, tert-butyl methyl ether, isopropyl ether, a $C_4$–$C_8$ ether, a $C_4$–$C_6$ ketone, dichloromethane, chloroform, dichloroethane, chlorobenzene or another chlorinated solvent, or pentane, hexane, cyclohexane, toluene, or another hydrocarbon or a binary or multiple mixture thereof.

14. A method according to claim 1, characterized in that the hydroxymandelic acids of the resin are eluted by means of an acid, base or a salt solution.

15. A method according to claim 14, characterized in that the acid is hydrochloric acid, sulphuric acid, $H_2CO_3$, carbon dioxide, sulphamic acid, phosphoric acid, boric acid, nitric acid, formic acid, acetic acid, chloroacetic acid, propionic acid, methanosulphonic acid, benzenesulphonic acid, p-toluenesulphonic acid, a $C_1$–$C_{14}$ organic acid or a mixture thereof.

16. A method according to claim 14, characterized in that the base is sodium hydroxide, potassium hydroxide, lithium hydroxide, ammonia, hydrazine, calcium hydroxide, methylamine, ethylamine, aniline, ethylenediamine, triethylamine, tetra ethyl ammonium hydroxide, a $C_2$–$C_{18}$ amine, a $C_4$–$C_{18}$ ammonium hydroxide, sodium methoxide, potassium methoxide, a $C_1$–$C_4$ organic base or a mixture thereof.

17. A method according to claim 14, characterized in that the salt is sodium bicarbonate, potassium bicarbonate, ammonium bicarbonate, sodium carbonate, potassium carbonate, ammonium carbonate, or a salt formed by the acids of claim 15 and the bases of claim 16.

18. A method according to claim 12 or 13, characterized in that the solution is water-based or solvent-based.

19. A method according to claim 1, characterized in that the 2-hydroxymandelic acid and the 4-hydroxymandelic acid are separated by means of selective elution.

20. A method according to claim 1, characterized in that the 4-hydroxymandelic acid and the 2-hydroxymandelic acid are eluted successively, using an eluent.

21. A method according to claim 1, characterized in that the 2-hydroxymandelic acid and 4-hydroxymandelic acid are selectively eluted by using two different eluents.

22. A method according to claim 1, characterized in that the 2-hydroxymandelic acid and 4-hydroxymandelic acid occur in the form of salt in the form of sodium, potassium, lithium, ammonium, methyl ammonium, tetramethyl ammonium, $C_2$–$C_{18}$ ammonium, ethylene diamine, magnesium, calcium, group II metal cation salt.

23. A method according to claim 1, characterized in that the separation of the 2-hydroxymandelic acid and 4-hydroxymandelic acid is performed by means of the simulated fluidized bed technique.

24. A method according to claim 1, characterized in that the phenol is used in a 1.1 to 6 equivalent excess in relation to the glyoxylic acid.

* * * * *